(12) United States Patent
Huculak et al.

(10) Patent No.: US 9,107,730 B2
(45) Date of Patent: Aug. 18, 2015

(54) OPTICAL COHERENCE TOMOGRAPHY AND ILLUMINATION USING COMMON LIGHT SOURCE

(75) Inventors: John Christopher Huculak, Mission Viejo, CA (US); Michael J. Yadlowsky, Sunnyvale, CA (US); Michael Papac, North Tustin, CA (US)

(73) Assignee: ALCON RESEARCH, LTD., Fort Worth, TX (US)

( * ) Notice: Subject to any disclaimer, the term of this patent is extended or adjusted under 35 U.S.C. 154(b) by 0 days.

(21) Appl. No.: 13/316,035

(22) Filed: Dec. 9, 2011

(65) Prior Publication Data

US 2012/0157828 A1 Jun. 21, 2012

Related U.S. Application Data

(60) Provisional application No. 61/421,578, filed on Dec. 9, 2010.

(51) Int. Cl.
*A61F 9/008* (2006.01)
*A61B 18/22* (2006.01)
(Continued)

(52) U.S. Cl.
CPC ............... *A61F 9/008* (2013.01); *A61B 18/22* (2013.01); *A61B 1/0638* (2013.01); *A61B 3/102* (2013.01); *A61B 5/0066* (2013.01)

(58) Field of Classification Search
CPC ...... A61B 18/22; A61B 3/102; A61B 5/0066; A61B 1/0638; A61F 9/008
USPC .......................................... 600/407, 473, 476
See application file for complete search history.

(56) References Cited

U.S. PATENT DOCUMENTS 4,449,535 A 5/1984 Renault
5,062,431 A 11/1991 Potter
(Continued)

FOREIGN PATENT DOCUMENTS

EP 1114608 A1 7/2001
JP 10286235 H 10/1998
(Continued)

OTHER PUBLICATIONS

Aguirre A.D., et al, "Continuum generation in a novel photonic crystal fiber for ultrahigh resolution optical coherence tomography at 800 nm and 1300 nm," Optics Express, Feb. 6, 2006, 1145-60, 14:3.
(Continued)

*Primary Examiner* — Katherine Fernandez
(74) *Attorney, Agent, or Firm* — Jason Finch

(57) ABSTRACT

A light source for a surgical system includes a broadband light source operable to produce broadband light. The light source further includes a wavelength splitter adapted to split the broadband light into illumination light having a spectral range covering at least a majority of the visible spectrum and surgical light having a spectral range outside of the spectral range of the illumination light. The light source then includes at least one surgical module adapted to control application of the surgical light. The light source also includes first and second coupling optics. The first coupling optics are configured to optically couple the illumination light to an illumination light guide for delivery to a first surgical probe. The second coupling optics are configured to optically couple the surgical light to a surgical light guide for delivery to a second surgical probe.

12 Claims, 4 Drawing Sheets

(51) Int. Cl.
*A61B 1/06* (2006.01)
*A61B 3/10* (2006.01)
*A61B 5/00* (2006.01)

(56) References Cited

U.S. PATENT DOCUMENTS

| | | |
|---|---|---|
| 6,183,086 B1 | 2/2001 | Neubert |
| 6,445,939 B1 | 9/2002 | Swanson et al. |
| 6,485,413 B1 * | 11/2002 | Boppart et al. ............... 600/160 |
| 6,813,050 B2 | 11/2004 | Chen et al. |
| 7,143,769 B2 | 12/2006 | Stoltz et al. |
| 7,261,687 B2 | 8/2007 | Yang |
| 7,364,543 B2 | 4/2008 | Yang et al. |
| 7,433,046 B2 | 10/2008 | Everett et al. |
| 7,783,346 B2 | 8/2010 | Smith et al. |
| 7,980,745 B2 | 7/2011 | Shanbaky |
| 2005/0259314 A1 * | 11/2005 | Tokuhisa et al. ............. 359/326 |
| 2008/0246920 A1 | 10/2008 | Buczek |
| 2009/0054957 A1 | 2/2009 | Shanbaky |
| 2009/0143772 A1 * | 6/2009 | Kurtz .............................. 606/4 |
| 2010/0056928 A1 * | 3/2010 | Zuzak et al. ................. 600/476 |
| 2010/0182569 A1 | 7/2010 | Artsyukhovich et al. |
| 2010/0228238 A1 | 9/2010 | Brennan et al. |
| 2010/0318074 A1 | 12/2010 | Dacquay et al. |

FOREIGN PATENT DOCUMENTS

| | | |
|---|---|---|
| JP | 2009519766 T2 | 5/2009 |
| JP | 2010178787 A2 | 8/2010 |
| WO | 03077746 A2 | 9/2003 |
| WO | 2009/094451 | 7/2009 |
| WO | 2009094451 | 7/2009 |

OTHER PUBLICATIONS

"Fiberoptic Illuminator (FI)," 510(k) Summary K062259 Premarket Notification, iScience Surg. Corp., May 3, 2006, 5 pages.

Gelikonov, V.M., et al, "Two-Wavelength Optical Coherence Tomography," Radiophys. & Quantum Electron., 2004, 848-859, 47:10-11.

Pan Y., et al, "Noninvasive Imaging of Living Human Skin With Dual-Wavelength Optical Coherence Tomography in Two and Three Dimensions," Journal of Biomedical Optics, Oct. 1998, 446-455, 3:4.

PCT International Search Report and Written Opinion for corresponding PCT/US2011/064064 with Apr. 4, 2012 mailing date, 8 pages.

Sacchet D., et al, "Simultaneous dual-band ultra-high resolution full-field optical coherence tomography," Optics Express, Nov. 24, 2008, 19434-446, 16:24.

Spöler F., et al, "Simultaneous dual-band ultra-high resolution optical coherence tomography," Optics Express, Aug. 20, 2007, 10832-841, 15:17.

Yaqoob Z et al., "Methods and application areas of endoscopic optical coherence tomography", Journal of Biomedical Optics, Nov./Dec. 2006, 11(6), 063001-1 thru 063001-19.

Nadeau et al., Laser-Pumped Endoscopic Illumination Source, 2059-62, Aug. 20-24, 2008, 30th Annual International IEE EMBS Conference.

European Examination Report for European Application No. 11802612.9 with mailing date May 21, 2014, 11 pages.

Xue P et al., Jul. 1, 2008 "Ultrahigh resolution optical coherence tomography with femtosecond Ti:sapphire laser and photonic crystal fiber", Chinese Science Bulletin, vol. 53, No. 13, 1963-1966.

* cited by examiner

OPTICAL COHERENCE TOMOGRAPHY AND ILLUMINATION USING COMMON LIGHT SOURCE

CROSS REFERENCE TO RELATED APPLICATION

This application claims priority under 35 U.S.C. §119 to U.S. Provisional Patent Application Ser. No. 61/421,578, filed Dec. 9, 2010, the entire contents of which are incorporated herein by reference.

BACKGROUND

1. Field of the Invention

Embodiments described herein relate to the field of microsurgical probes. More particularly, embodiments described herein are related to the field of surgical illumination using broadband light sources, and more particularly, to the use of supercontinuum lasers in illumination and surgical applications.

2. Description of Related Art

The field of microsurgical procedures is evolving rapidly. Typically, these procedures involve the use of probes that are capable of reaching the tissue that is being treated or diagnosed. Such procedures make use of endoscopic surgical instruments having a probe coupled to a controller device in a remote console. Current state of the art probes are quite complex in operation, often times requiring moving parts that are operated using complex mechanical systems. In many cases, an electrical motor is included in the design of the probe. Most of the prior art devices have a cost that makes them difficult to discard after one or only a few surgical procedures. Furthermore, the complexity of prior art devices leads generally to probes having cross sections of several millimeters. These probes are of little practical use for ophthalmic microsurgical techniques. In ophthalmic surgery, dimensions of one (1) mm or less are preferred, to access areas typically involved without damaging unrelated tissue.

Scanning mechanisms that allow time-dependent direction of light for diagnostic or therapeutic purposes have been used in endoscopic surgical instruments. These instruments typically use probes that provide imaging, treatment, or both, over an extended area of tissue without requiring motion of the endoscope relative to its surroundings. However, there are typically multiple probes for each function, and different light sources are used for different applications.

Therefore, there is a need for a common light source useful for multiple functions that provides effective illumination in small-scale probes.

SUMMARY

According to particular embodiments of the present invention, a light source for a surgical system includes a broadband light source operable to produce broadband light. The light source further includes a wavelength splitter adapted to split the broadband light into illumination light having a spectral range covering at least a majority of the visible spectrum and surgical light having a spectral range outside of the spectral range of the illumination light. The light source then includes at least one surgical module adapted to control application of the surgical light. The light source also includes first and second coupling optics. The first coupling optics are configured to optically couple the illumination light to an illumination light guide for delivery to a first surgical probe. The second coupling optics are configured to optically couple the surgical light to a surgical light guide for delivery to a second surgical probe. Various embodiments of the present invention also include methods of use and operation and surgical systems including a common light source for illumination light and surgical light.

According to other embodiments of the present invention, an surgical system for providing illumination includes a broadband coherent light source, coupling optics, and a nano-scale light guide connectable to a surgical probe. The broadband coherent light source produces broadband coherent light having a spectral range including at least a majority of the visible spectrum. The coupling optics couple the broadband coherent light to the nano-scale light guide with a high numerical aperture, thus producing a large angular distribution when the broadband light is emitted from a distal end of the optical fiber.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

Various embodiments of the present invention provide a common light source adapted for use with multi-function surgical probes, particularly ophthalmic surgical probes. Other embodiments of the present invention provide a multi-function surgical probe adapted to deliver light from a common light source to provided an integrated multi-function surgical probe. In particular embodiments, the multiple function of the surgical probe include optical coherence tomography (OCT) scanning and visible illumination for visualization of a surgical site.

The probe may be a hand-held probe, for direct manipulation by specialized personnel. In some embodiments, the probe may be designed to be controlled by a robotic arm or a computer-controlled device. Probes have a proximal end close to the operation controller (be it a specialist or a device), and a distal end, close to or in contact with the tissue. Probes according to embodiments disclosed herein may have small dimensions, be easy to manipulate from a proximal end, and minimally invasive to the surrounding tissue. In the distal end, the probe ends with a tip, from where the probe performs certain action on a target tissue located in the vicinity of the tip. For example, the probe may deliver light from its tip, and receive light reflected or scattered from the tissue, coupled through the tip. The tip of the probe may include movable elements that enable the tip to perform its action.

Figure 1:
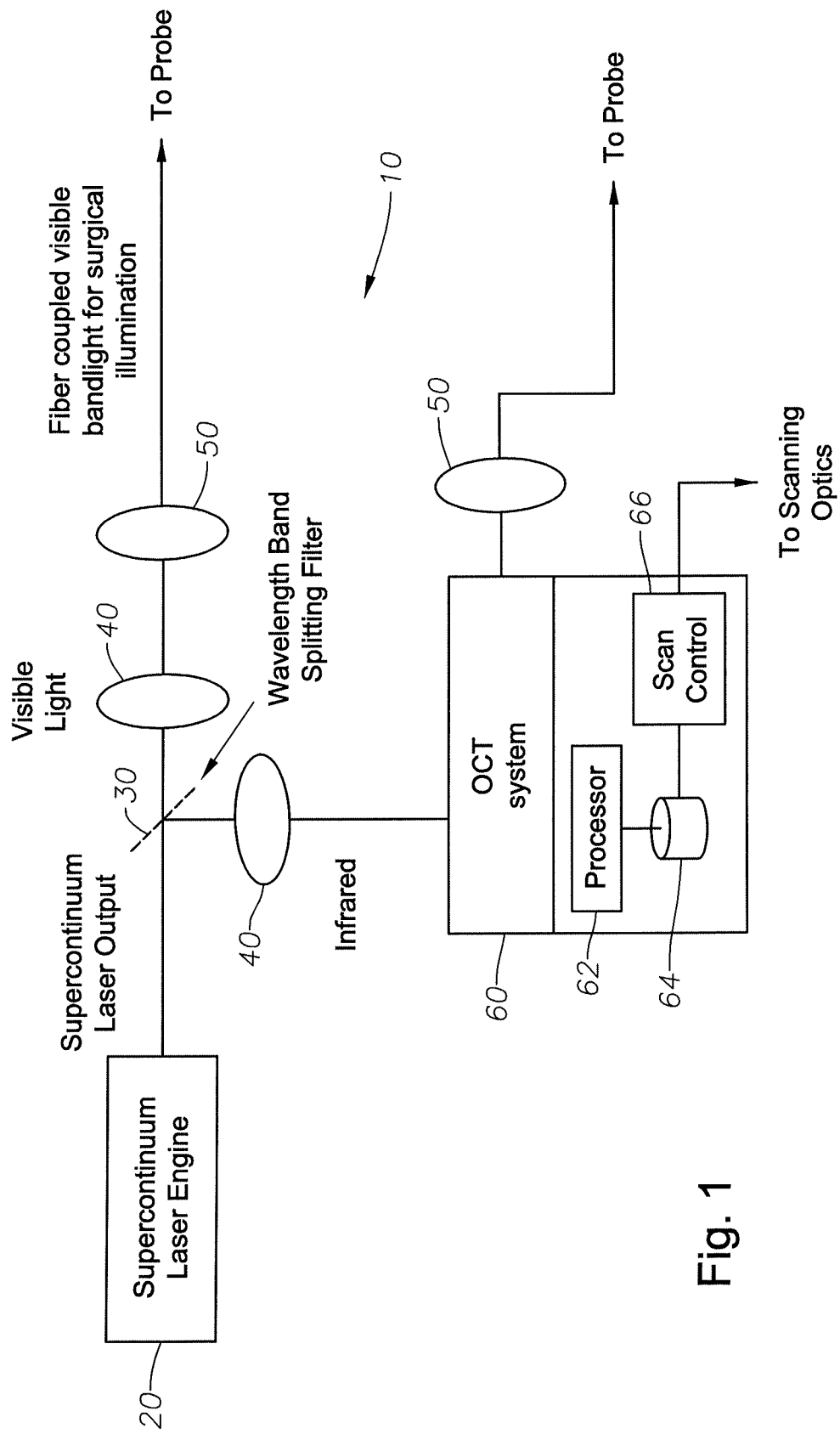
FIG. 1 is a block diagram of a surgical system including a broadband light source according to a particular embodiment of the present invention.

FIG. 1 is a block diagram of a surgical system 10 including a broadband light source 20 according to a particular embodiment of the present invention. In the depicted embodiment, the broadband light source 20 is coupled to separate ports of a multi-function surgical probe 100. In alternative embodiments, there may be one or more additional surgical probes 100 corresponding to different functions using light from the broadband light source 20. As described in detail below, the broadband light source 20 generates light in a wavelength range that includes wavelengths distributed broadly over the visible spectrum, as contrasted with narrow-bandwidth lines at a few discrete wavelengths so that the majority of wavelengths in the visible spectrum are not present, in order to provide illumination. The broadband light source 20 also generates light in at least one wavelength range outside of the spectrum used in illumination that is suitable for a particular surgical application. Thus, for example, infrared radiation could be used for OCT applications. Typical wavelength bands used for OCT applications include wavelengths around 820-870 nm, 1060 nm, or 1300 nm. The particular wavelength band might be selected for compatibility with light guides, relative performance characteristics under certain operating conditions, or other similar considerations. In another example, high energy blue or ultraviolet radiation could be used for tissue modification or other treatment applications. In general, any suitable combination of broadband illumination and other light outside of the illumination spectrum may be employed.

In particular embodiments, the broadband light source 20 may be a supercontinuum laser. Supercontinuum lasers are laser sources including a dispersion medium to distribute a narrow-band laser pulse across a wide range of wavelengths, which can include the visible spectrum. One drawback of having such a broad spectral distribution used for illumination is that considerable energy can be included in the non-visible wavelengths. Energy in the blue and ultraviolet wavelengths can be particularly harmful to ocular tissue within the eye, which is ordinarily protected from wavelengths in the ultraviolet range by the absorption characteristics of the natural lens. Likewise, infrared radiation can be easily absorbed by ocular tissue to produce undesired heating of tissue. For safety reasons, it is therefore desirable to filter out the non-visible wavelengths from a supercontinuum laser source used for illumination, meaning that this energy is wasted and the overall efficiency of the system is reduced.

Various embodiments of the present invention utilize energy that would otherwise be lost by dividing light into illumination light within a visible wavelength range and surgical light used for a surgical operation within at least a surgical target area illuminated by the illumination light. In the embodiment depicted in FIG. 1, the broadband light source 20 includes a wavelength splitter 30 that divides broadband light into at least two different spectral components, at least one of which spans a wavelength range including the majority of the visible spectrum suitable for "white light" surgical illumination.

The broadband light source 20 also includes beam conditioning elements 40 that alter the energy level of the illumination light and the surgical light and/or filter out remaining wavelengths that are superfluous or undesirable in order to produce respective light beams with desired energy and wavelength characteristics. In particular embodiments, the wavelength splitter 30 and/or the beam conditioning elements 40 may include selectors, such as switches or electronic controls, which permit a user to select a desired band of surgical light for difference applications. Thus, for example, different infrared bands might be selectable for OCT. In another example, there might be a selection between a wavelength used for OCT and a wavelength used for treatment. This could be useful, for example, to perform a treatment on tissue and then to verify that the treatment had been performed completely and successfully.

The broadband light source further includes coupling interfaces 50 that couple the illumination light and the surgical light into either a light guide or a surgical light module that is in turn coupled to one or more probes 100. The coupling interfaces 50 include optical elements adapted to allow surgical light and illumination light to be effectively delivered to the target site. In the case of illumination light, the broad spectral band for "white light" illumination requires a relatively wide spectral range to be carried without substantial losses. Likewise, it is desirable to minimize losses to brightness, so that it is desirable to have a high numerical aperture when coupling to a light guide, such as an optical fiber. The high numerical aperture also provides a wide angular distribution of light emitted from the illumination fiber, which in turn allows a smaller diameter fiber to be used effectively.

Surgical light used for OCT uses a relatively narrower spectral band, so that a single mode fiber may be adequate. But because of the axial precision needed for accurate OCT measurements, a low dispersion optical fiber is typically used, and the optical fiber must also be suitable for carrying the longer-wavelength infrared radiation without losses. As this example illustrates, the optical fiber and associated coupling optics 50 will ordinarily be different for the surgical light and the illumination light from the same source. Alternatively, the illumination light and surgical light could be adapted in order to allow both forms of light to be delivered through a common light guide. This would require the coupling optics 50 for the common light guide to be adapted so that the illumination light and surgical light did not interfere with one another and, in applications like OCT, to allow various wavelengths of surgical light to be separated from the return beam. It might also be less desirable for illumination light to be scanned with surgical light used for OCT or other surgical applications, so that there might need to be a splitter placed before the scanning optics to redirect illumination light outside of the scanning path. In contrast with various embodiments of the present invention, conventional surgical probes have not addressed these problems associated with using a common light source.

In the depicted embodiment, an OCT engine 60 is illustrated as an example of a surgical module. The OCT engine 60 is an interferometry apparatus for measuring the interference between a reference beam generated using the surgical light and light returning from the tissue illuminated by the surgical light. In particular embodiments, the OCT engine 60 may include a spectrometer-based interferometer, also known as "spectral domain OCT." This refers to an OCT system that uses a relatively broad spectral range of light and measures interference of discrete wavelengths within the spectral band to reconstruct information about the target tissue. Such applications are particularly suitable with broadband light source 20 because the surgical light from the broadband light source 20 will already include a large number of wavelengths.

The OCT engine 60 also includes a processor 62, which may be one or more suitable electronic components for processing information, including but not limited to a microprocessor, microcontroller, application-specific integrated circuit (ASIC), or other programmable device. The processor 62 processes information about the interference produced by light reflected from the tissue to generate a mathematical representation of the scanned tissue, which may in turn be used to produce an electronic image of the tissue. The OCT engine 60 also includes a memory 64, which may be any suitable form of information storage including electronic, magnetic, or optical storage that may be either volatile or non-volatile. Finally, the OCT engine 60 includes a scan controller 66. The scan controller 66 may be any suitable combination or hardware, software, and/or firmware and mechanical components, which may include processor 62 and memory 64, suitable for controlling the movement of optical components to redirect the surgical light used by the OCT engine 60. For example, in embodiments where a probe 100 includes scanning optics for the OCT beam, the scan controller 66 may be connected to the scanning optics in order to control the scanning mechanism.

In one example of OCT imaging techniques, a light beam having a coherence length may be directed to a certain spot in the target tissue by using a probe. The coherence length provides a resolution depth, which when varied at the distal end of the probe may be de-convolved to produce an in-depth image of the illuminated portion of the tissue (A-scan). A 2-dimensional tissue image may be obtained through a B-scan. In some embodiments, B-scans are straight lines along a cross-section of the tissue. Furthermore, by performing repeated B-scans along different lines in the tissue, a 3D rendition of the tissue may be provided. In some embodiments, the B-scans may be a set of lines having the same length and arranged in a radius from a common crossing point. Thus, the plurality of B-scans provides an image of a circular area in the tissue, having a depth.

In some embodiments, OCT techniques use forward-directed scan procedures. In this case, optical illumination takes place in the forward direction of the probe longitudinal axis. In forward-directed scans, the target tissue may be ahead of the probe in a plane perpendicular to the probe longitudinal axis. Thus, light traveling from the tip of the probe to the tissue, and back from the tissue into the probe may travel in a direction substantially parallel to the probe longitudinal axis. In some embodiments using forward-directed scans, the target tissue may be approximately perpendicular to the probe longitudinal axis, but not exactly. Furthermore, in some embodiments light traveling to and from the target tissue from and into the probe may not be parallel to the probe longitudinal axis, but form a symmetric pattern about the probe longitudinal axis. For example, light illuminating the target tissue in a forward-directed scan may form a solid cone or a portion thereof about the probe longitudinal axis. Likewise, light collected by an endoprobe in a forward-directed scan may come from target tissue in a 3D region including a portion of a cone section around the probe longitudinal axis.

Figure 2:
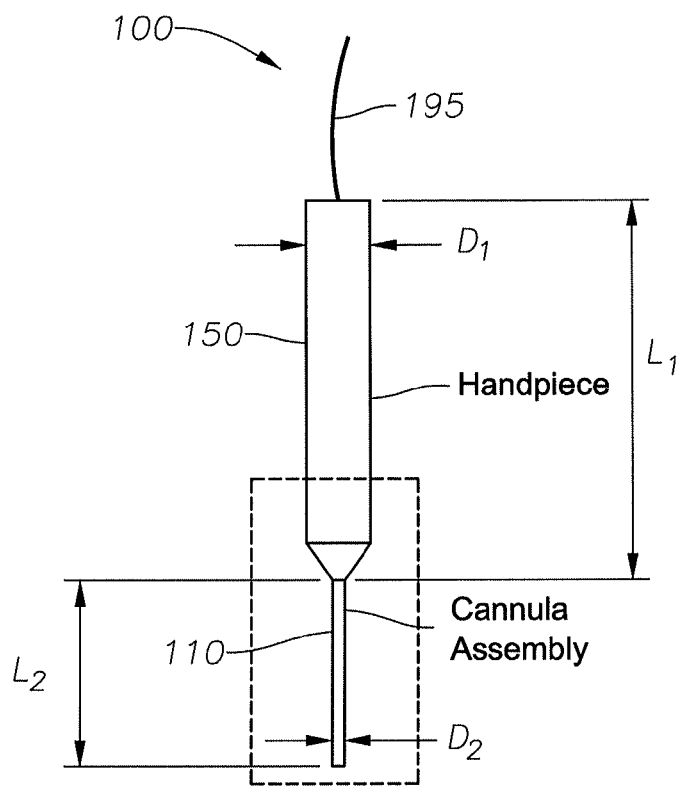
FIG. 2 illustrates a microsurgical endoprobe including an optical scanning element, a hand-piece, and ports coupling to light guides from the broadband light source according to some embodiments.

FIG. 2 shows microsurgical endoprobe 100 that includes a cannula assembly 110 and a hand-piece housing 150. A cannula assembly 110 includes the distal end of endoprobe 100 which may be elongated along the probe longitudinal axis and have a limited cross-section. For example, in some embodiments cannula assembly 110 may be about 0.5 mm in diameter ($D_2$) while hand-piece 150 may have a substantially cylindrical shape of several mm in diameter ($D_1$) such as 12-18 mm. A coupling cable 195 includes light guides carrying light from the coupling optics 50 of the broadband light source 20. In alternative embodiments, separate probes 100 could be coupled to the common light source, or both surgical light and illumination light could be coupled into a common light guide.

In some embodiments, assembly 110 may be in contact with tissue, including target tissue for the microsurgical procedure. Thus, assembly 110 may be coated with materials that prevent infection or contamination of the tissue. Furthermore, surgical procedures and protocols may establish hygienic standards for assembly 110, all of which are incorporated herein by reference in their entirety. For example, it may be desirable that assembly 110 be disposed of after used once. In some situations, assembly 110 may be disposed of at least every time the procedure is performed on a different patient, or in a different part of the body.

Hand-piece housing 150 may be closer to the proximal end of the probe, and may have a larger cross section as compared to element 110. Element 150 may be adapted for manual operation of endoprobe 100, according to some embodiments. Element 150 may be adapted for robotic operation or for holding by an automated device, or a remotely operated device. While assembly 110 may be in contact with living tissue, element 150 may not be in direct contact with living tissue. Thus, even though element 150 may comply with hygienic standards, these may be somewhat relaxed as compared to those used for assembly 110. For example, element 150 may include parts and components of endoprobe 100 that may be used repeatedly before disposal.

Thus, some embodiments of endoprobe 100 as disclosed herein may include complex components in element 150, and less expensive, replaceable components may be included in assembly 110. Some embodiments may have a removable element 110 which is disposable, while hand-piece 150 may be used more than once. Hand-piece 150 may be sealed hermetically, in order to avoid contamination of the tissue with particulates or fumes emanating from internal elements in hand-piece 150. In some embodiments, cannula assembly 110 may be fixed to hand-piece 150 by an adhesive bonding. According to other embodiments, assembly 110 may be removable from hand-piece 150, to allow easy replacement of endoprobe 100 for repeated procedures. Some embodiments consistent with FIG. 2 may have a disposable element 150 and a disposable assembly 110.

In some embodiments, an OCT technique may use side imaging. For example, in side imaging the target tissue may be parallel to a plane containing the probe longitudinal axis. In a situation like this, it may be desirable to move the illumination spot in a circular trajectory around the probe longitudinal axis, to create a closed-loop image of the target tissue. Such a situation may arise in microsurgery involving endovascular procedures. For example, in coronary angiography the interior wall of the coronary artery may be fully scanned in cylindrical sections along the arterial lumen using embodiments described herein.

Figure 3:
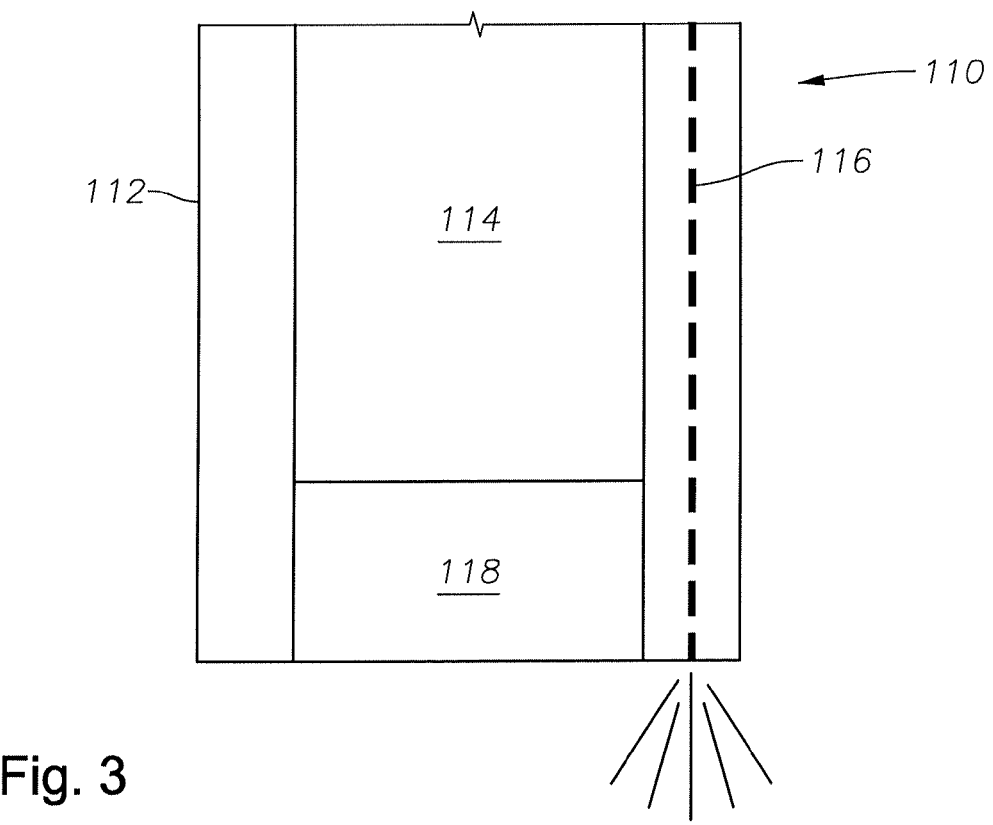
FIG. 3 is a schematic cross-section for a distal end of a microsurgical endoprobe such as the one shown in FIG. 2.

FIG. 3 is a schematic illustrating particular features of the cannula assembly 110 of an example endoprobe 100 according to particular embodiments of the present invention. In the depicted embodiment, the cannula assembly 110 includes a cannula 112 surrounding an OCT fiber 114. The cannula 112 may be formed from any suitable material for insertion into an incision during surgical operations, such as stainless steel. A groove or channel may be formed into the cannula to receive an illumination fiber 116. The illumination fiber 116 may be of considerable smaller diameter than the OCT fiber 114.

In the depicted embodiment, the cannula assembly 110 includes scanning optics 118 placed at a distal end of the cannula assembly 110. The scanning optics 118 include optical elements movable in any suitable manner to scan the optical beam. The scanning optics 118 may include, for example, counter-rotating gradient index (GRIN) lenses used to scan a measurement beam across a target area. The illumination fiber 116 in the cannula 112 bypasses the scanning optics 118 so that the illumination is not scanned with the measurement OCT beam. This advantageously allows separate illumination and surgical light to be easily used within the same probe 100.

Figure 4:
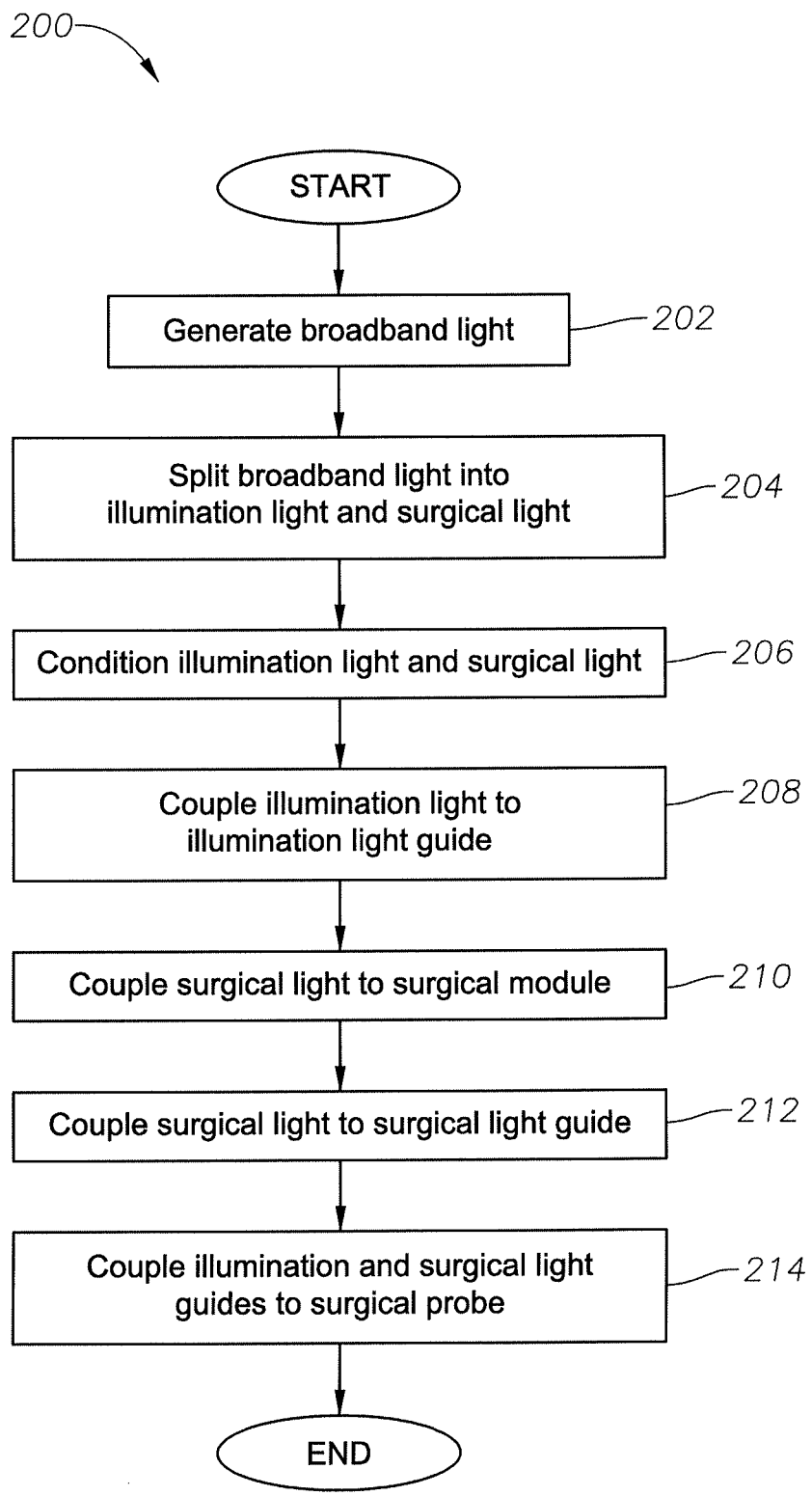
FIG. 4 is a flowchart illustrating an example method of generating light for illumination and surgical applications using a common light source.

FIG. 4 is a flowchart 200 illustrating an example method generating light for illumination and surgical applications using a common light source. At step 202, broadband light that includes illumination light and surgical light is generated. As noted above, illumination light in this context refers to light covering at least a majority of the visible light spectrum, suitable for "white light" illumination of a surgical target site. Surgical light refers to light outside the spectral band of the illumination light that is also delivered at or near the illuminated surgical field. At step 204, the broadband light is split into illumination light and surgical light. At step 206, the beams of illumination light and surgical light are conditioned. For example, the light may be filtered to removed undesired wavelengths, the beam uniformity may be improved, or other beam properties may be suitably adjusted for compatibility with the end application.

The illumination light is coupled to an illumination light guide using first coupling optics at step 208. This may be, for example, a small diameter optical fiber, wherein the illumination light is coupled to the optical fiber with a high numerical aperture to produce a wide angular distribution when the illumination light is emitted. The surgical light is coupled to a surgical module that controls the application of the surgical light for tissue treatment or characterization at step 210. At step 212, the surgical light is coupled to a surgical light guide using second coupling optics. At step 214, both the illumination light guide and the surgical light guide are coupled to a surgical probe. The probe may then be disposed near a surgical target site for selective surgical use.

In certain embodiments of the invention, the wavelength of the surgical light may be selectable by a user, so that different wavelengths or wavelength ranges can be used for different applications. For example, a surgeon might use OCT wavelengths to characterize tissue, then switch to a treatment wavelength to treat the tissue, then return to the OCT wavelength to verify that the treatment was successfully performed. In general, any method of use or operation consistent with the various embodiments disclosed herein may be employed with such embodiments.

Figure 5:
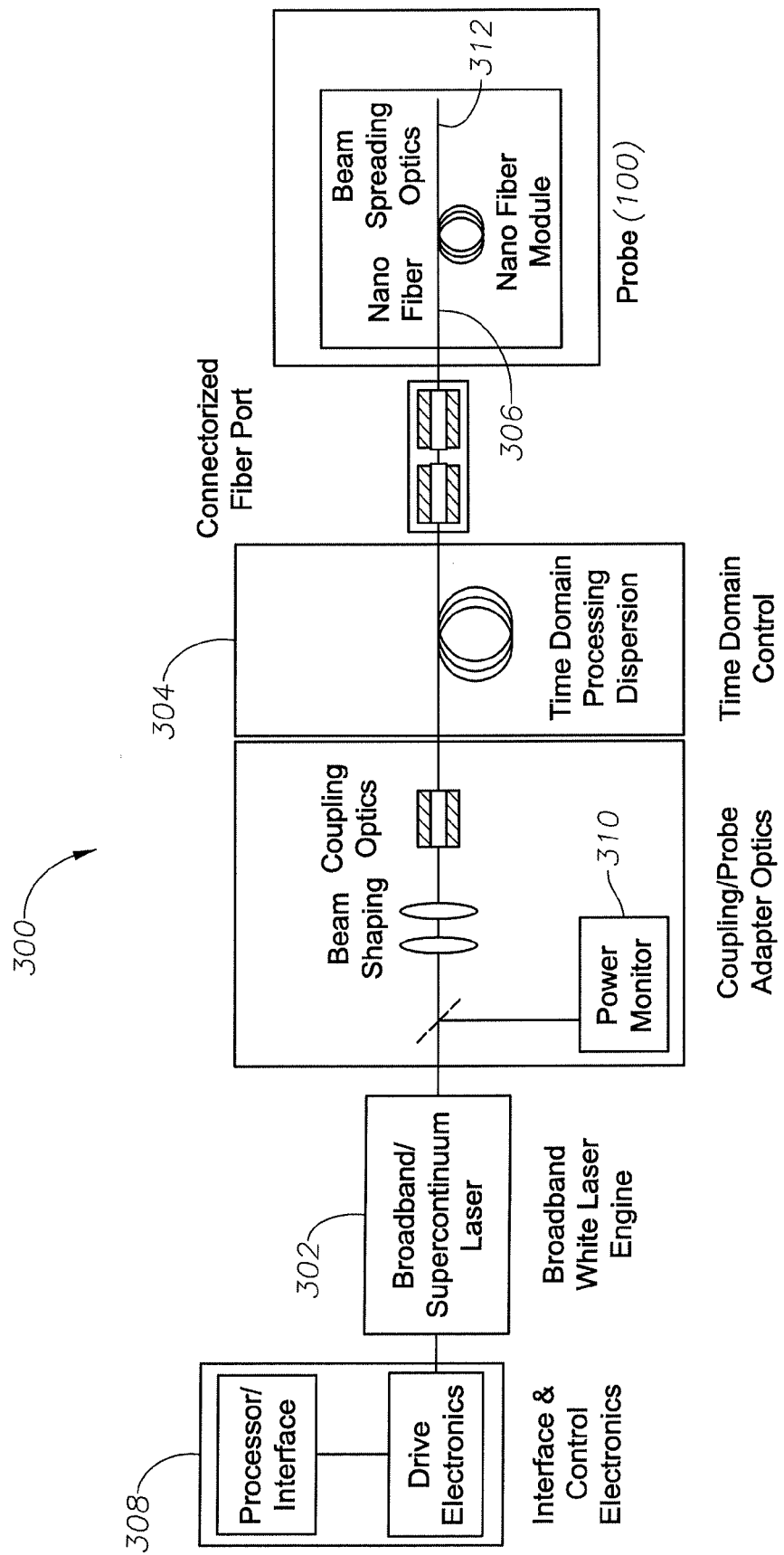
FIG. 5 is a block diagram of a supercontinuum laser source that may be used as a broadband light source according to various embodiments of the present invention.

FIG. 5 illustrates an example of a broadband laser source 20 in the form of a supercontinuum light source 300. The supercontinuum light source includes a supercontinuum laser 302, which produces broadband laser energy by delivering high energy laser pulses to a dispersive, non-linear medium, such as a photonic crystal fiber. This effectively broadens the spectral distribution of the pulse. The supercontinuum laser 302 may also include control electronics and/or interface 308 and the beam power can be monitored by a power monitor 310 in order to maintain broadband pulse quality. In illumination applications, it may also be desirable to further stretch the pulses in the time domain using another dispersive medium 304, which may in turn be part of a light guide 306 that is connectable to a surgical probe, such as probe 100. Other beam conditioning, such as filtering out undesired or harmful wavelengths, may also be performed.

Preferably, the spatial coherence of the supercontinuum beam can be exploited so that the light guide 306 is a nano-scale light guide 306 having a diameter (or other largest cross-sectional dimension) of less than 100 microns. In particular, a nano-scale light guide with a high numerical aperture, such as a fiber with a large difference between the refractive index of the core and the refractive index of the cladding, may be employed so that there is a wide angular distribution of emitted light. An alternative would be to taper the tip shape of the nano-scale light, such as by forming it into a compound parabolic concentrator, in order to produce a wide distribution angle. Beam spreading optics 312 may also be used to widen the angular distribution of emitted light. While it could be difficult or impossible to produce an adequate angular distribution from such small light guides with incoherent white light, the coherence of the supercontinuum laser permits both sufficient illumination (on the order of 5-15 lumens) along with sufficient angular distribution to illuminate a relatively wide surgical field.

Various embodiments of the present invention provide illumination and surgical light to a surgical target area using a common light source. Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. A surgical system, comprising:
   a broadband light source configured to produce broadband light;
   a wavelength splitter configured to split the broadband light into illumination light having a spectral range covering at least a majority of the visible spectrum and surgical light having a spectral range outside of the spectral range of the illumination light;
   an Optical Coherence Tomography (OCT) engine configured to control application of the surgical light; and
   illumination and surgical coupling optics, the illumination coupling optics configured to optically couple the illumination light to an illumination light guide for delivery to an illumination probe and the surgical coupling optics configured to optically couple the surgical light to a surgical light guide for delivery to a surgical probe.

2. The surgical system of claim 1, wherein the illumination and surgical probes are integrated into a single hand-piece housing.

3. The surgical system of claim 2, wherein a cannula assembly of the integrated illumination and surgical probes has a diameter of 0.5 mm or less.

4. The surgical system of claim 3, wherein the cannula assembly includes scanning optics for scanning a beam of the surgical light across a target surgical site.

5. The surgical system of claim 1, wherein the illumination and surgical probes have separate hand-piece housings.

6. The surgical system of claim 1, wherein the broadband light source is a supercontinuum laser.

7. The surgical system of claim 1, wherein the surgical light has a spectral range in the infrared range.

8. The surgical system of claim 1, wherein the surgical probe is an OCT probe.

9. The surgical system of claim 1, wherein the surgical light has a spectral range in the ultraviolet range.

10. The surgical source of claim 1, wherein the spectral range of the surgical light is selectable from among at least two different spectral ranges.

11. The surgical source of claim 10, wherein the at least two different spectral ranges comprise a first range for optical coherence tomography and a second range for surgical treatment of tissue.

12. The surgical source of claim 1, wherein the OCT engine includes a spectral domain interferometer.

* * * * *